United States Patent
Nellenbach

(10) Patent No.: US 10,647,535 B2
(45) Date of Patent: May 12, 2020

(54) METHODS FOR MANUFACTURING PRINTED LAMINATES

(71) Applicant: The Procter & Gamble Company, Cincinnati, OH (US)

(72) Inventor: Eva G. Nellenbach, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 190 days.

(21) Appl. No.: 15/912,625

(22) Filed: Mar. 6, 2018

(65) Prior Publication Data

US 2019/0276260 A1 Sep. 12, 2019

(51) Int. Cl.

| | |
|---|---|
| *B32B 41/00* | (2006.01) |
| *B65H 23/04* | (2006.01) |
| *B32B 38/18* | (2006.01) |
| *B32B 38/00* | (2006.01) |
| *B32B 17/10* | (2006.01) |
| *B65H 23/188* | (2006.01) |
| *B32B 7/12* | (2006.01) |
| *B32B 37/14* | (2006.01) |
| *B65H 23/02* | (2006.01) |
| *A61F 13/513* | (2006.01) |

(Continued)

(52) U.S. Cl.
CPC ..... *B65H 23/046* (2013.01); *A61F 13/51394* (2013.01); *B32B 7/12* (2013.01); *B32B 17/10256* (2013.01); *B32B 37/144* (2013.01); *B32B 38/0004* (2013.01); *B32B 38/0012* (2013.01); *B32B 38/145* (2013.01); *B32B 38/1833* (2013.01); *B32B 41/00* (2013.01); *B65H 23/0204* (2013.01); *B65H 23/1886* (2013.01); *A61F 13/15699* (2013.01); *A61F 13/15707* (2013.01); *A61F 13/536* (2013.01); *A61F 2013/1591* (2013.01); *A61F 2013/15243* (2013.01); *B29L 2031/4878* (2013.01); *B32B 2038/0028* (2013.01); *B32B 2041/04* (2013.01)

(58) Field of Classification Search
CPC ...... A61K 31/165; A61K 31/196; A61K 9/06; A61K 9/08; A61K 47/10; A61K 9/0014; A61K 31/60; A61K 31/352; A61K 45/06; A61K 31/513; A61K 31/35; A61K 31/618; A61K 31/125; A61K 31/05; A61K 31/045; A91K 31/351
USPC .......................... 156/64, 350, 351, 378, 379
See application file for complete search history.

(56) References Cited

U.S. PATENT DOCUMENTS 6,033,502 A * 3/2000 Coenen ............. A61F 13/15772
156/229

* cited by examiner

*Primary Examiner* — Michael N Orlando
*Assistant Examiner* — Joshel Rivera
(74) *Attorney, Agent, or Firm* — Christian M. Best

(57) ABSTRACT

Methods for manufacturing printed laminates or elastic printed laminates are disclosed. The printed laminates may have a first extensible material and a second extensible material. The first extensible material may have a plurality of repeating graphic sets each having a repeating graphic set length. The first extensible material may have a first strain and the second extensible material may have a second, different strain. The second strain may be constant. The first strain may be variable to correspond to the repeating graphic set lengths to a predetermined laminate pitch. The first and second extensible material may be joined together at a point of joinder. An elastic member, such as a plurality of elastic strands, for example, may be positioned intermediate the first and second extensible materials to form an elastic laminate.

20 Claims, 9 Drawing Sheets

(51) Int. Cl.
*A61F 13/15* (2006.01)
*A61F 13/536* (2006.01)
*B29L 31/48* (2006.01)

METHODS FOR MANUFACTURING PRINTED LAMINATES

FIELD

The present disclosure is directed to methods for manufacturing printed laminates, and is more specifically directed to, methods for manufacturing printed laminates on an absorbent article manufacturing line.

BACKGROUND

Absorbent articles are used to contain bodily exudates (e.g., urine, bowel movements, and menses) in infants, children, teens, and adults. Some absorbent articles comprise printed laminates as components thereof. The components may be backsheet films and outer cover nonwoven laminates, waist belt laminates, ear or side panel laminates, and/or other laminates. Some of these laminates may comprise one or more nonwoven materials, one or more films, and optionally an elastic member, such as a plurality of elastic strands or an elastic film, for example. An example laminate in a form of a waist belt laminate may have a first nonwoven material, a second nonwoven material, and a plurality of elastic strands positioned intermediate the first and second nonwoven materials. One of the materials (e.g., film or nonwoven) may comprise a repeating graphic set. During manufacturing, a roll of material with a plurality of the repeating graphics sets may be combined with another roll of material to form a printed laminate. One problem with such a process is that the material with the plurality of repeating graphics sets needs to be aligned with the one or more other materials of the laminate in a machine direction to a predetermined laminate pitch so that a full repeating graphics set appears in a produced component (e.g., a waist belt laminate) or so that excessive waste does not need to be trimmed from a produced component. If only part of a repeating graphics set appears in a produced component (e.g., only half or a portion of a logo or graphic set), absorbent article perceived quality by consumers may go down. Also, if excessive waste needs to be removed from a produced laminate, costs may increase. As such, methods for manufacturing printed laminates that register repeating graphics sets on one material of a laminate with other materials of the laminate are required to improve consumer perceptions of product quality and to reduce excessive waste and, thereby reduce costs.

SUMMARY

The present disclosure provides methods for manufacturing printed laminates. More particularly, the present disclosure provides methods for manufacturing printed laminates on an absorbent article manufacturing line that solve the problems identified above. Through the methods of the present disclosure, the produced laminates may have repeating graphics sets that are registered with predetermined laminate pitches. As such, the produced laminates may each have a full repeating graphics set that is not cut off and that does not need to be excessively trimmed. This may be accomplished by adjusting/varying the machine direction strain in one or more materials of the laminate, for example the material with the plurality of repeating graphic sets. Before the adjusting/varying step, a repeating graphic set length in a first material may be sensed as the first material is conveyed in a machine direction using a suitable sensor. The sensor may then compare the sensed repeating graphic set length to a predetermined laminate pitch. The predetermined laminate pitch is the required length of the laminate being produced. The sensor may then send a signal to a first strain adjusting device (e.g., a driven roll) for the first material, such that the first strain adjusting device may increase or decrease the first strain in the first material to lengthen or shorten the repeating graphic set length and make it correspond to the predetermined laminate length. "Correspond(s)" may mean, but does not necessarily mean, that the repeating graphic set length is about equal to (e.g., +/−1% of a predetermined laminate pitch) or equal to the predetermined laminate pitch. "Correspond(s)" may instead mean that the repeating graphic set length fits within the predetermined laminate pitch such that the repeating graphic set length is smaller than the predetermined laminate pitch. After the repeating graphic set length corresponds to the predetermined laminate pitch (by increasing or decreasing the machine direction tension on the first material), the first and second materials (or other materials) may be joined together to form the printed laminate. The printed laminates may or may not have an elastic member intermediate the first and second materials. The elastic member may comprise a plurality of elastic strands, for example.

The present disclosure is directed, at least in part, to a method for manufacturing a printed laminate on an absorbent article manufacturing line. The method may comprise conveying a first extensible material toward a point of joinder in a machine direction while straining the first material in the machine direction at a first strain. The first extensible material may comprise a plurality of repeating graphic sets. The plurality of repeating graphic sets may each comprise a repeating graphic set length. The method may comprise separately, conveying a second extensible material toward the point of joinder in the machine direction while straining the second material in the machine direction at a second strain. The second strain may be different than or greater than the first strain. The method may comprise measuring at least some of the plurality of repeating graphic set lengths using a sensor upstream of the point of joinder while the first extensible material is under the first strain. The method may comprise comparing the repeating graphic set length to a predetermined laminate pitch, adjusting the first strain until the repeating graphic set length corresponds to the predetermined laminate pitch, and joining the first material and the second material at the point of joinder to form a printed laminate comprising the first extensible material and the second extensible material. The method may comprise conveying an elastic member, such as a plurality of elastic strands, toward and through the point of joinder intermediate the first extensible material and the second extensible material to form an elastic printed laminate. The elastic member may be attached to the first or second extensible materials through the use of adhesives or bonding, for example.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

DETAILED DESCRIPTION

Various non-limiting forms of the present disclosure will now be described to provide an overall understanding of the principles of the structure, function, manufacture, and use of the methods for manufacturing printed laminates disclosed herein. One or more examples of these non-limiting forms are illustrated in the accompanying drawings. Those of ordinary skill in the art will understand that the methods of manufacturing printed laminates specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Figure 1:
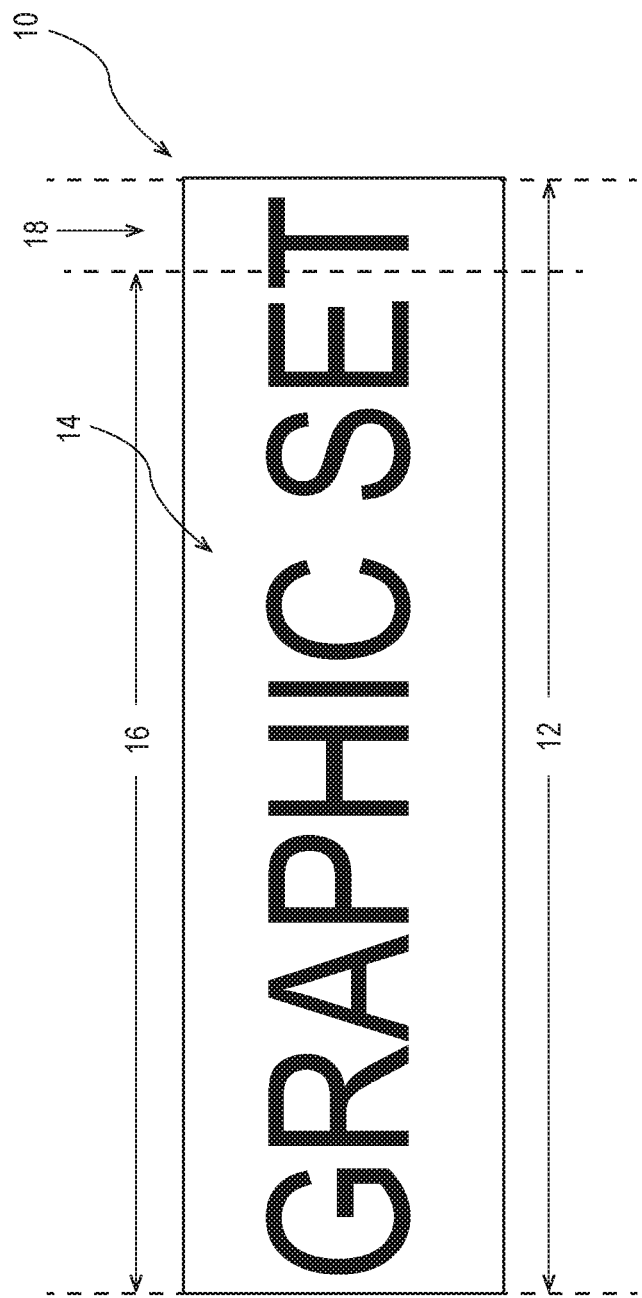
FIG. 1 is a plan view of a related art printed laminate where a repeating graphic set length in a first material is greater than a predetermined laminate pitch of a produced laminate.

FIG. 1 is a plan view of a related art printed laminate 10 where a repeating graphic set length 12 in a first material 14 is greater than a predetermined laminate pitch 16 of a produced laminate. In the instance of FIG. 1, the area 18 outside of the predetermined laminate pitch 16 must be trimmed away from the produced laminate to produce a suitably sized produced laminate. This creates waste and increases costs and also cuts off a portion of the graphics possibly leading to the consumer perception of poor quality.

Figure 2:
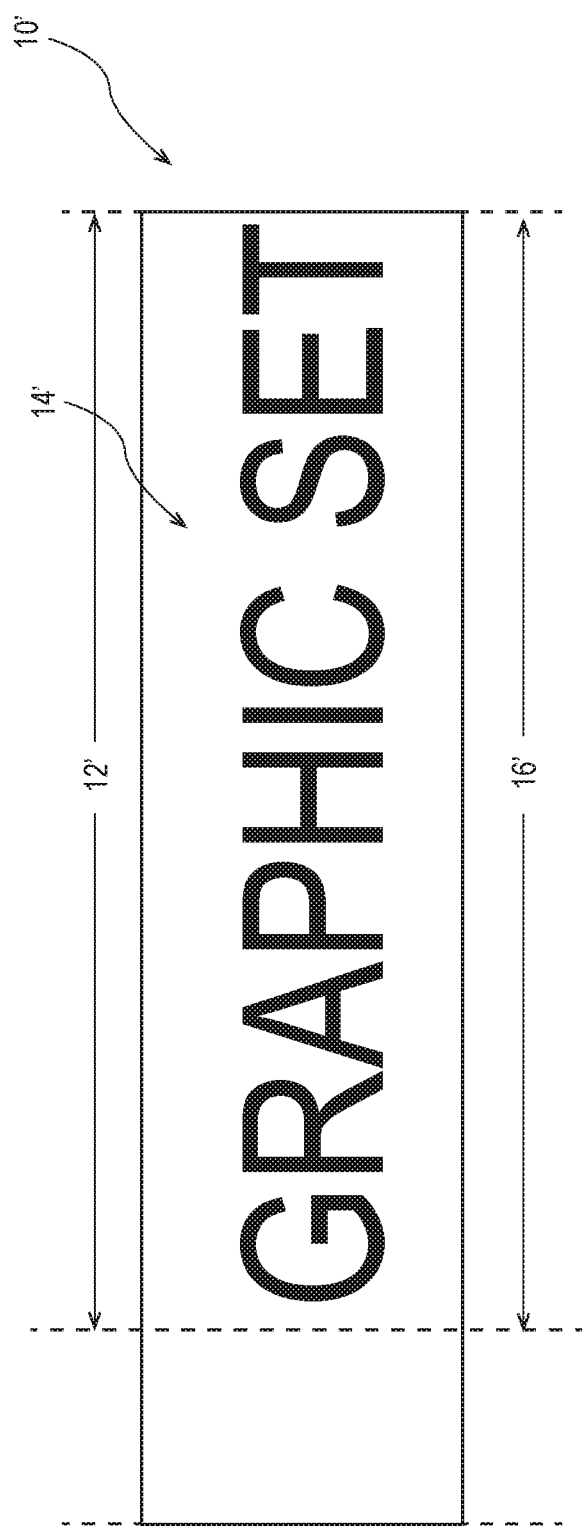
FIG. 2 is a plan view of a related art printed laminate where a repeating graphic set length in a first material is less than a predetermined laminate pitch of a produced laminate.

FIG. 2 is a plan view of another related art printed laminate 10' where a repeating graphic set length 12' in a first material 14' is less than a predetermined laminate pitch 16' of a produced laminate. In such an instance, the repeating graphic set is offset from the center in the produced laminate. This may lead to the consumer perception of poor quality.

The present disclosure is directed, in part, to methods of manufacturing printed laminates so that a repeating graphic set length in a first extensible material corresponds to a predetermined laminate pitch of a produced laminate, thereby increasing consumer perceptions of high quality and reducing waste, and thereby costs.

Figure 3:
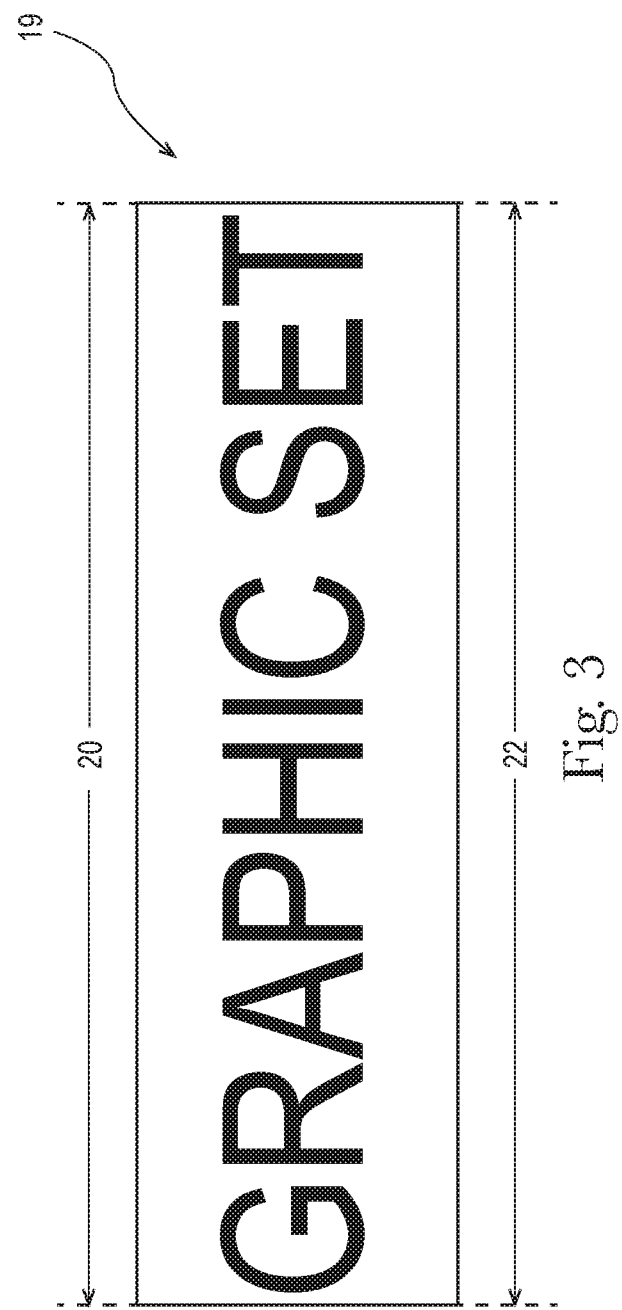
FIG. 3 is a plan view of a printed laminate of the present disclosure where a repeating graphic set length corresponds to a predetermined laminate pitch of a produced laminate.

FIG. 3 is a plan view of a printed laminate 19 of the present disclosure where a repeating graphic set length 20 corresponds (as defined herein) to a predetermined laminate pitch 22 of a produced laminate. The printed laminate 19 may be made according to the methods described herein. The printed laminate 19 may reduce costs by eliminating or reducing trim, thereby reducing waste. The printed laminate 19 may also increase consumer perceptions of high quality by having repeating graphics sets that are centered, or substantially centered, on the produced laminates. In other instances, the repeating graphic set length 20 may be smaller than the predetermined laminate pitch 22, but may be centered within the predetermined laminate pitch 22 to aid in the consumer perception of high quality.

Figure 4:
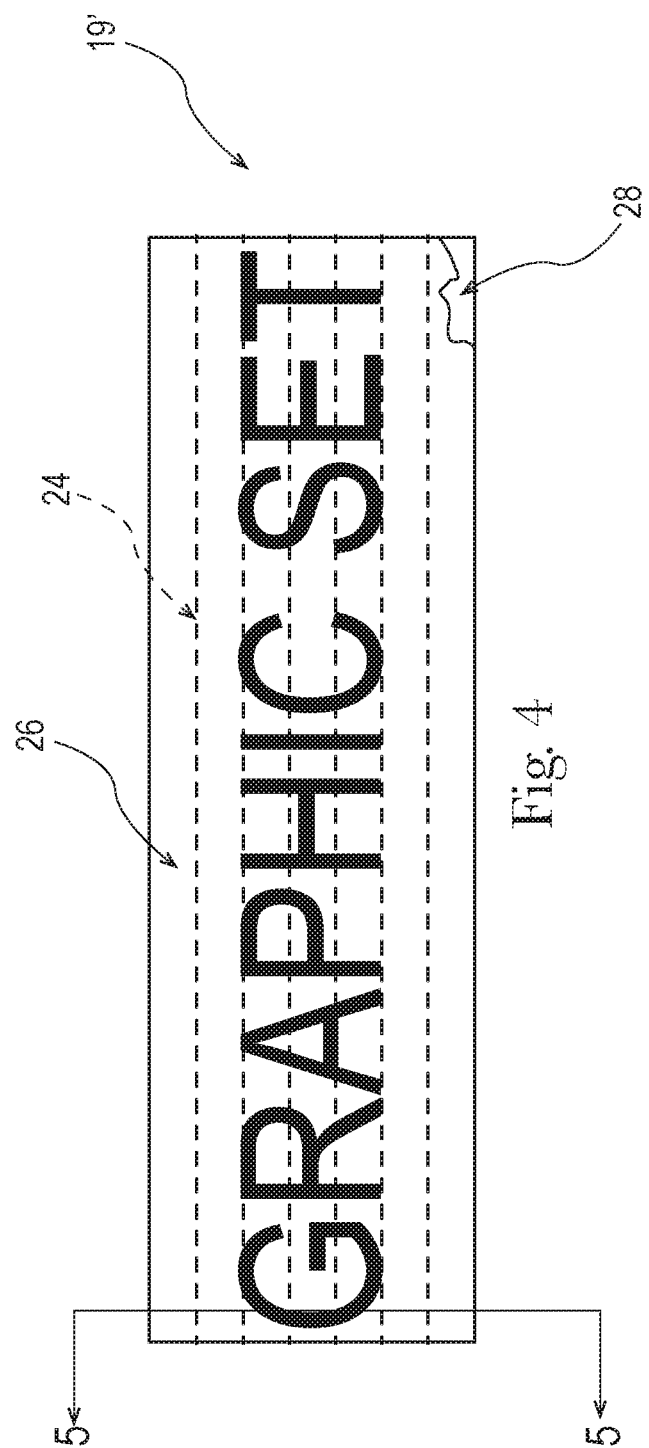
FIG. 4 is a plan view of a printed laminate of the present disclosure where a repeating graphic set length corresponds to a predetermined laminate pitch of a produced laminate with elastic strands.
Figure 5:
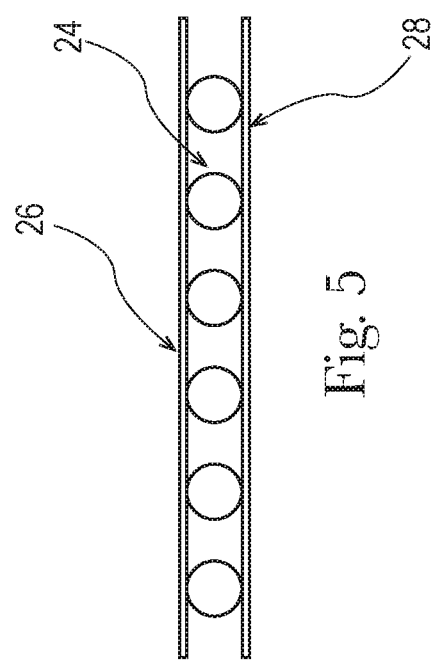
FIG. 5 is a cross-sectional illustration of the produced laminate of FIG. 4, taken about line 5-5 of FIG. 4.

FIG. 4 is a plan view of a printed laminate 19' of the present disclosure where a repeating graphic set length corresponds to a predetermined laminate pitch of a produced laminate, wherein the printed laminate 19' comprises an elastic member, such as a plurality of elastic strands 24 or an elastic film, a first material 26, and at least a second material 28. FIG. 5 is a cross-sectional illustration of the printed laminate 19' of FIG. 4, taken about line 5-5 of FIG. 4.

In regard to FIGS. 4 and 5, the first material 26 may be extensible and may comprise one or more films, one or more nonwovens, a film and a nonwoven, or other suitable materials. "Extensible" means the material is capable of being stretched in the machine direction and then is able to return to its initial machine direction dimension or substantially to its initial machine direction dimension. The second material may or may not be extensible and may comprise one or more films, one or more nonwovens, a film and a nonwoven, or other suitable materials. As one example, the first and second materials may both be nonwoven materials, one material may be a nonwoven material and the other material may be a film, or both of the materials may be a film.

Figure 6:
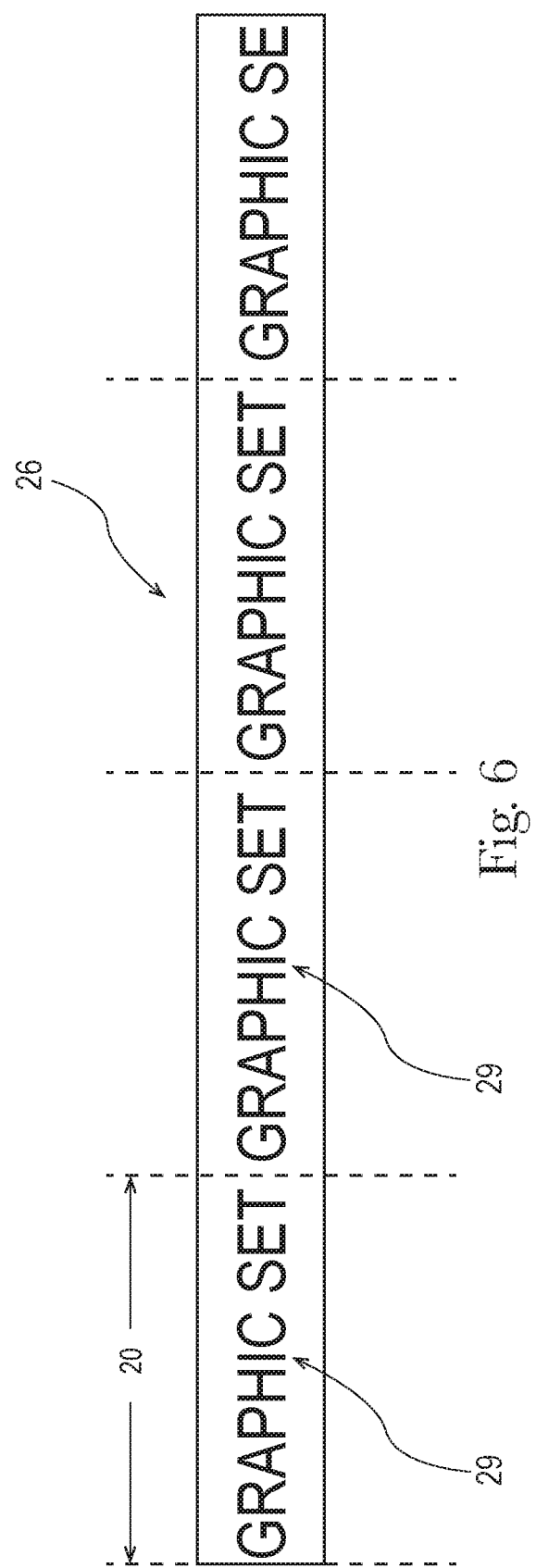
FIG. 6 is a plan view of a first extensible material comprising a plurality of repeating graphic sets, each repeating graphic set having a repeating graphic set length.

FIG. 6 is a plan view of a first extensible material 26 comprising a plurality of repeating graphic sets 29, each repeating graphic set 29 having a repeating graphic set length 20. The repeating graphic set lengths 20 may be increased or decreased depending on the predetermined laminate pitch. As such, the repeating graphic set length 20 may be increased for a larger predetermined laminate pitch or decreased for a smaller predetermined laminate pitch by adjusting the first strain (machine direction) in the first extensible material 26 before the first extensible material 26 is joined to the second material 28, as will be described further below.

The "graphic set" illustrated in FIGS. 1-4 and 6 may be any suitable graphics. Some examples include brand names, brand icons, objects, shapes, animals, and/or numbers, for example. Each graphic set may be continuous or discontinuous. For example, in a discontinuous configuration, a heart may be on a left side of the graphic set, a word or brand name may be in the middle, and another heart may be on a right side. Together, these elements may form a graphic set. As another example, in a continuous configuration, a word may make up the entire graphic set. The graphic sets in a first extensible material may all be the same or may be different. In other instances, the same graphic sets may repeat at different intervals in a first extensible material.

Figure 7:
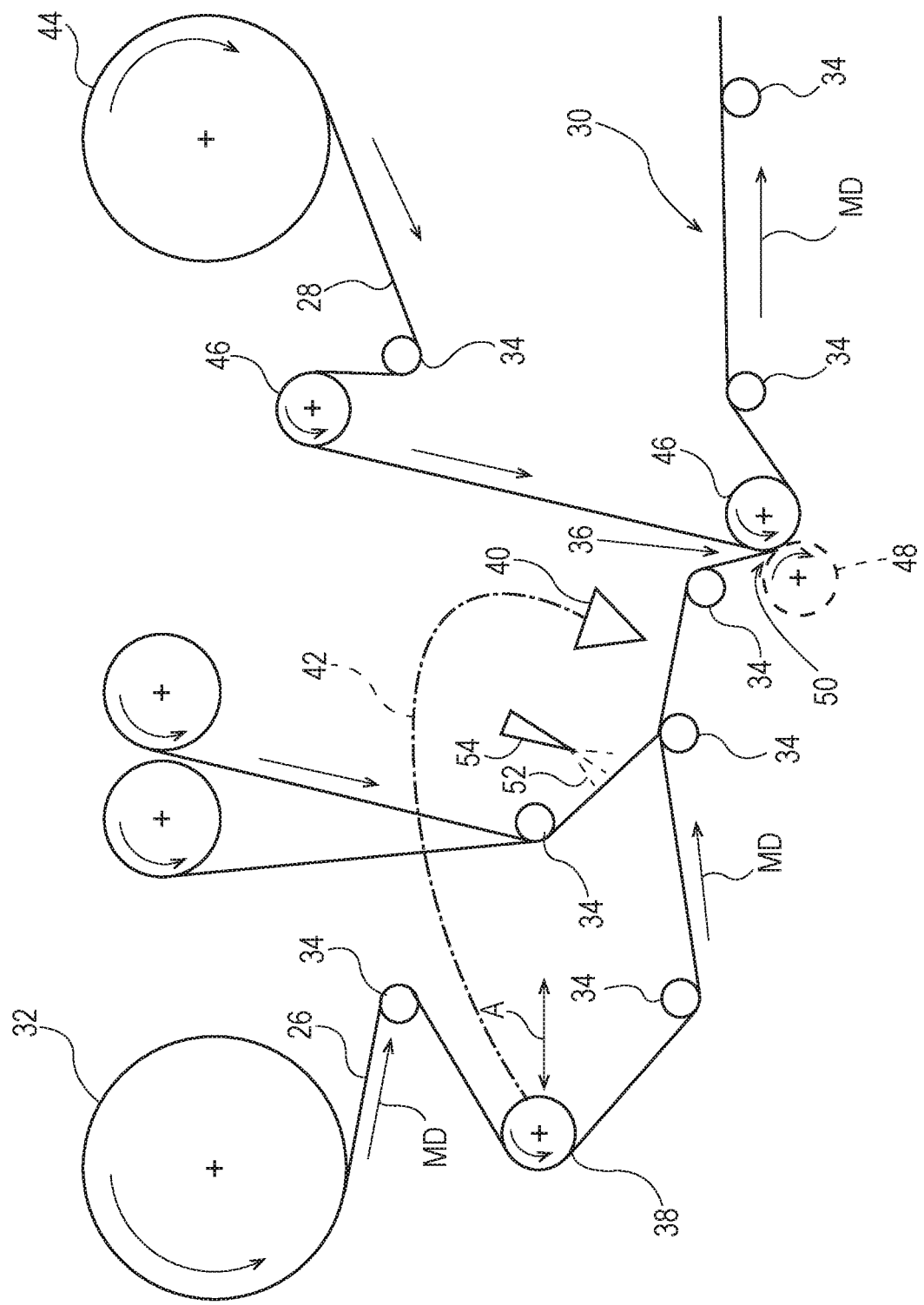
FIG. 7 is a schematic illustration of a method of manufacturing a printed laminate of a first extensible material and a second material to form a web of produced laminates.

FIG. 7 is a schematic illustration of a method of manufacturing a printed laminate of a first extensible material and a second (optionally extensible) material to form a web of produced laminates 30 having repeating graphics set lengths that correspond to predetermined laminate pitches. The first extensible material 26 may comprises a plurality of repeating graphic sets, each comprising a repeating graphic set length, as described above. The first extensible material 26 may be unwound from a first roll 32. The first roll 32 may have a core with the first extensible material 26 being wrapped around the core, much like a roll of toilet tissue. The core may engage a driven support pin configured to rotate (in the direction indicated by the arrow) and unwind the first extensible material 26 from the first roll 32.

The first extensible material 26 may be conveyed at over a plurality of idler or driven rolls or guide bars 34 toward a point of joinder 36 between the first extensible material 26 and the second extensible or non-extensible material 28. The first extensible material 26 may also be conveyed over a variable speed roller 38 upstream of the point of joinder 36. The variable speed roller 38 may be configured to increase or decrease the machine direction first strain on the first extensible material 26 upstream of and/or at the point of joinder 36. The variable speed roller 38 may rotate in the direction illustrated in FIG. 7. The variable speed roller 38 may vary its rotational speed in response to a signal from a sensor 40 measuring at least some of, or all of, the plurality of the repeating graphic set lengths 20. A suitable sensor may be an LR-W70C sensor from Keyence America. Once the sensor 40 measures the plurality of the repeating graphic set lengths 20 being conveyed past itself, the sensor 40 may then compare the repeating graphic set lengths 20 to a predetermined laminate pitch 22 for the produced laminate 30. The predetermined laminate pitch 22 will be set based on what size laminates are currently being manufactured. If the repeating graphic set length 20 is measured to be larger than the predetermined laminate pitch 22, the sensor 40 may send a signal 42 (indicated by a dashed line in FIG. 7) to the variable speed roller 38 to increase its rotational speed and, thereby decrease the first strain in the first extensible material to reduce (i.e., shorten) the repeating graphic set length 20 so that it corresponds to the predetermined laminate pitch 22. If the repeating graphic set length 20 is measured to be smaller than the predetermined laminate pitch 22, the sensor 40 may send a signal (hard wired, electronically, or otherwise) to the variable speed roller 38 to decrease its rotational speed and, thereby increase the first strain in the first extensible material 26 to increase (i.e., lengthen) the repeating graphic set length 20 so that it corresponds to the predetermined laminate pitch 22. The first roll 32 may feed the first extensible material 26 toward the variable speed roller 38 at a constant linear speed. The first extensible material 26 may be wrapped around the variable speed roller 38 more or less than illustrated in FIG. 7.

Instead of increasing or decreasing the rotational speed of the variable speed roller 38, the roller 38 may rotate at a constant rotational speed and the adjustment to the first strain may be made by moving the roller 38 in the directions of arrow A. The closer the roller 38 moves to the right in FIG. 7, the more the first strain is decreased (i.e., a shorter repeating graphic set length 20) in the first extensible material 26. The further the roller 38 moves to the left in FIG. 7, the more the first strain in the first extensible material 26 is increased (i.e., a longer repeating graphic set length 20). In this context, a guide bar may also be used instead of the roller 38.

The second material 28 may be conveyed toward the point of joinder 36. The second material 28 may be wound on a second roll 44. The second roll 44 may have a core with the second extensible material or second material 28 being wrapped around the core, much like a roll of toilet tissue. The core may engage a driven support pin configured to rotate (in the direction indicated by the arrow) and unwind the second extensible material or material 26 from the second roll 44. The second material 28 may be conveyed over a plurality of idler or driven rollers or guide bars 34 towards the point of joinder 36. The second material 28 may also be conveyed over a second roller 46. The second roller 46 may rotate about its rotational axis at a constant rotational speed in the direction indicated by the arrow in FIG. 7. As such, the second material 28 may be conveyed toward the point of joinder 36 at a constant machine direction second strain.

At the point of joinder 36, the first extensible material 26 may be combined with the second material 28 when passing over a joinder roll 46. The joinder roll 46 may rotate in the direction indicated by the arrow in FIG. 7. The first extensible material 26 may be adhesively attached to the second extensible or non-extensible material 28 by applying adhesive to one or both of the first or second materials 26, 28. Adhesive 52 may be applied through the use of an adhesive applicator 54, such as an adhesive sprayer. Other methods of joining two webs, such as bonding or ultrasonic bonding, for example, are also within the scope of the present disclosure. Optionally, an anvil roll 48 may be positioned proximate to the joinder roll 46 to aid in joining the first and second materials 26, 28 together. The anvil roll 48 may rotate in the direction indicated by the arrow in FIG. 7. If the anvil roll 48 is provided, the anvil roll 48 and the joinder roll 46 may form a nip 50 therebetween through which the first and second material 26, 28 (and optionally an elastic member) may be conveyed.

An elastic member, such as a plurality of elastic strands 56 or one or more elastic films, may be conveyed toward the point of joinder 36. Only two elastic strands 56 are illustrated in FIG. 7 for simplicity, but it is to be understood that any suitable number of elastic strands 56 may be conveyed toward the point of joinder 36, such as 5 to 50, for example. The elastic strands 56 or films may be unwound from elastic rolls 58. The elastic rolls 58 may rotate in the direction illustrated in FIG. 7. The elastic strands 56 may be conveyed toward and through the point of joinder 36 intermediate the first extensible material 26 and the second material or second extensible material 28. The elastics strands 56 may be used to form an elastic printed laminate 30, such as a front or rear elastic waist belt for a pant-type absorbent article.

The machine direction second strain of the second extensible material 28 may be different than or greater than the machine direction first strain of the first extensible material 26. The machine direction second strain may be different than the machine direction first strain in the range of about 0.2% to about 10%, about 0.2% to about 6%, about 0.4% to about 4%, or about 0.5% to about 3%, for example. The machine direction first strain on the first extensible material may be in the range of about 0% to about 7%, about 0% to about 5%, or about 0% to about 2.5%. The machine direction second strain on the second extensible material may be in the range of about 0.2% to about 10%, 0.4% to about 6%, about 0.5% to about 4%, or about 0.5% to about 3%, for example. Other strains for the first and second strains are envisioned depending on the requirements of a produced laminate.

Methods of Manufacturing Printed Laminates

A method for manufacturing a printed laminate on an absorbent article manufacturing line is provided. The method may comprise conveying a first extensible material toward a point of joinder (i.e., a point where the first and second extensible materials are joined to each other or overlapped with each other) in a machine direction while straining the first material in the machine direction at a first strain. The first extensible material may comprise a plurality of repeating graphic sets. The plurality of repeating graphic sets may each comprise a repeating graphic set length. The method may comprise separately (e.g., from a different spool or location), conveying a second extensible material toward the point of joinder in the machine direction while straining the second material in the machine direction at a second strain. The second strain may be different than the first strain. The method may comprise measuring at least some of the plurality of repeating graphic set lengths using a sensor upstream of the point of joinder while the first extensible material is under the first strain. The method may comprise comparing the repeating graphic set length or lengths to a predetermined laminate pitch. The method may comprise adjusting the first strain (i.e., reducing or increasing) until the repeating graphic set length corresponds to the predetermined laminate pitch. The method may comprise joining the first extensible material and the second extensible material at the point of joinder to form a printed laminate comprising the first extensible material and the second extensible material. The method may comprise conveying an elastic member, such as a plurality of elastic strands, toward and through the point of joinder intermediate the first extensible material and the second extensible material to form an elastic printed laminate. The elastic printed laminate may be used as a front or rear waist belt in a pant-type absorbent article, for example.

The first and second extensible materials may comprise one or more nonwoven materials, one or more films, and/or one or more other suitable materials. In an example, the first and second extensible materials may both comprise a nonwoven material or more than one nonwoven material.

The first strain of the first extensible material may be in the range of about 0% to about 2.5% (or other first strains described herein). The second strain of the second extensible material may be in the range of about 0.5% to about 3% (or other second strains described herein).

The second strain of the second extensible material may be different than, or greater than, the first strain of the first extensible material by at least 0.5% and less than 3% (or other ranges described herein).

The second strain of the second extensible material may be constant (including process tolerances, e.g., 3 m/s constant speed may vary between 2.9 m/s and 3.1 m/s, but is planned to be 3 m/s). The first strain may be variable to adjust the repeating graphic set length (i.e., shorten or lengthen).

The method may comprise applying adhesive to the elastic member, to the first extensible material, and/or to the second extensible material upstream of the point of joinder.

The method may comprise conveying the first extensible material over a roller upstream of the point of joinder. The adjusting of the first strain step may comprise varying the rotational speed of the roller to increase or decrease the first strain of the first extensible material to shorten or lengthen the repeating graphic set length.

The method may comprise cutting the printed produced laminate to the predetermined laminate pitch. If an elastic member is provided intermediate the first and second extensible materials, the method may comprise cutting the elastic printed laminate to the predetermined laminate pitch. The method may comprise joining the printed laminate or elastic printed laminate with a portion of an absorbent article chassis (in a waist belt context).

A method for manufacturing a printed laminate on an absorbent article manufacturing line is provided. The method may comprise conveying a first extensible material toward a point of joinder in a machine direction while straining the first material in the machine direction at a first strain. The first extensible material may comprise a plurality of repeating graphic sets. The plurality of repeating graphic sets may each comprise a repeating graphic set length. The method may comprise separately, conveying a second extensible material toward the point of joinder in the machine direction while straining the second material in the machine direction at a second strain. The second strain may be different than or greater than the first strain. The method may comprise measuring at least some of the plurality of repeating graphic set lengths using a sensor upstream of the point of joinder while the first extensible material is under the first strain. The method may comprise comparing the repeating graphic set length to a predetermined laminate pitch, adjusting the first strain until the repeating graphic set length corresponds to the predetermined laminate pitch, conveying a plurality of elastic strands toward the point of joinder; and joining the first material and the second material at the point of joinder to form a printed elastic laminate comprising the first extensible material, the second extensible material, and the plurality of elastic strands. The plurality of elastic strands may be positioned intermediate the first extensible material and the second extensible material.

The method may comprise conveying the first extensible material over a roller upstream of the point of joinder. The adjusting of the first strain step may comprise varying the rotational speed of the roller to increase or decrease the first strain to shorten or lengthen the repeating graphic set length. The first extensible material may comprise one or more nonwoven materials and the second extensible material may comprise one or more nonwoven materials. The second strain may be constant. The first strain may be variable to adjust the repeating graphic set length.

A method for manufacturing a printed laminate on an absorbent article manufacturing line is provided. The method may comprise conveying a first extensible nonwoven material toward a point of joinder in a machine direction while straining the first material in the machine direction at a first strain. The first extensible nonwoven material may comprise a plurality of repeating graphic sets. The plurality of repeating graphic sets may each comprise a repeating graphic set length. The method may comprise separately, conveying a second extensible nonwoven material toward the point of joinder in the machine direction while straining the second material in the machine direction at a second strain. The second strain may be different than or greater than the first strain. The second strain may be constant. The method may comprise measuring at least some of the plurality of repeating graphic set lengths using a sensor upstream of the point of joinder while the first extensible material is under the first strain. The method may comprise comparing the repeating graphic set length to a predetermined laminate pitch, adjusting the first strain until the repeating graphic set length corresponds to the predetermined laminate pitch, conveying a plurality of elastic strands toward the point of joinder; and joining the first material and the second material at the point of joinder to form a printed elastic laminate comprising the first extensible material, the second extensible material, and the plurality of elastic strands. The plurality of elastic strands may be positioned intermediate the first extensible material and the second extensible material.

Absorbent Articles

The printed laminates, with or without elastic members or elastic strands, may form portions of absorbent articles. Absorbent articles may comprise taped diapers, pants, adult incontinence diapers or pads, sanitary napkins, panty liners, and/or other suitable absorbent articles. The printed laminates may also be useful in other consumer products. In an absorbent article context, the printed laminates may form an outer cover nonwoven material and a backsheet film, a topsheet and an acquisition layer, a dual layer topsheet, an ear laminate, a topsheet and a secondary topsheet, a waist belt laminate, and/or may form other suitable absorbent article components.

Figure 8:
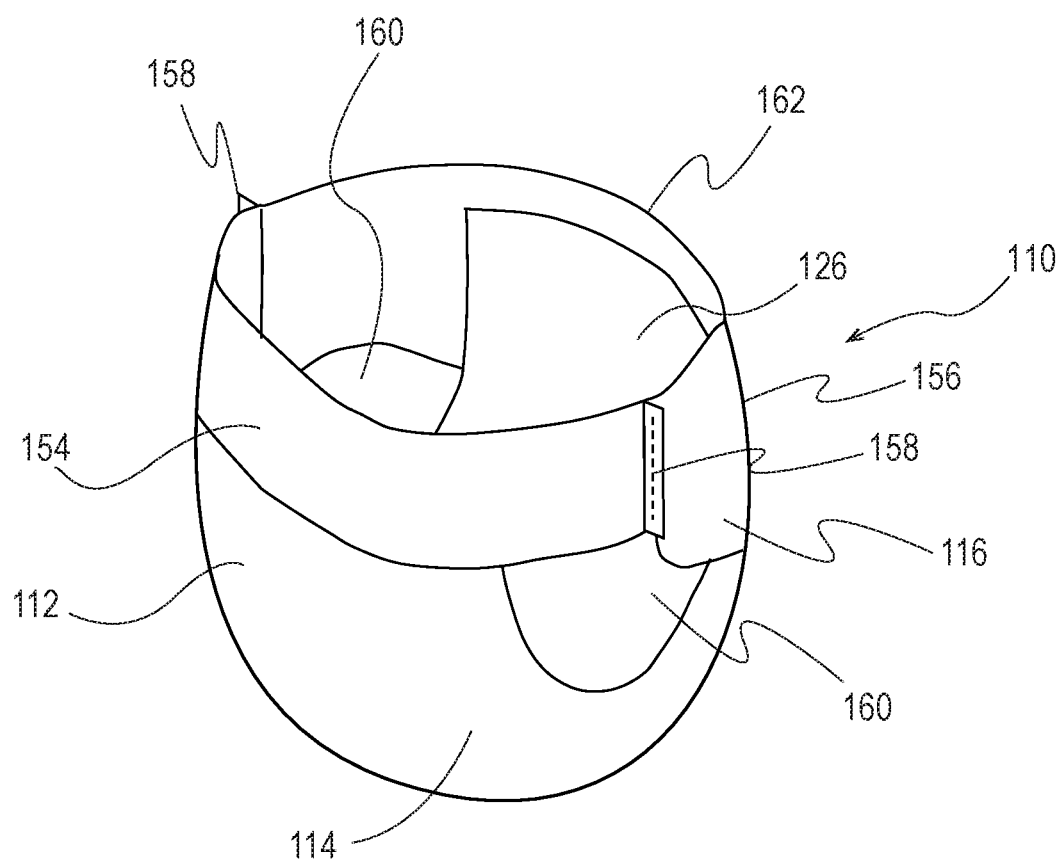
FIG. 8 is a front perspective view of an absorbent article comprising one or more printed laminates of the present disclosure.
Figure 9:
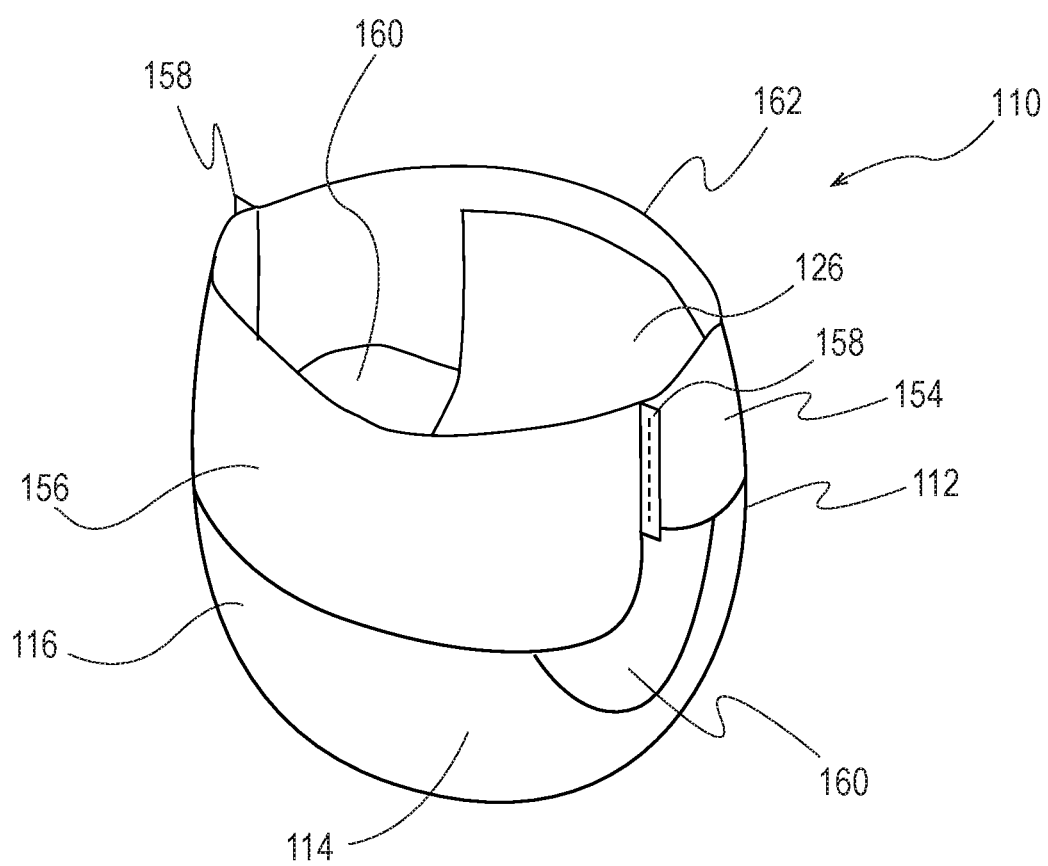
FIG. 9 is a back perspective view of the absorbent article comprising one or more printed laminates of the present disclosure.

FIGS. 8 and 9 illustrate an example absorbent article in the form of a pant. The pant may comprise the printed laminates of the present disclosure, as for example, one or more waist belts of the pant. FIG. 8 is a front perspective view of an absorbent article comprising one or more printed laminates of the present disclosure. FIG. 9 is a back perspective view of the absorbent article comprising one or more printed laminates of the present disclosure.

Referring again to FIGS. 8 and 9, an absorbent article 110 in the form of a belted pant is illustrated. The absorbent article 110 comprises a front region 112, a crotch region 114, and a back region 116. The absorbent article may comprise a central chassis 126 extending at least between the front region 112 and the back region 116. The absorbent article 110 may define leg openings 160 and comprise a front waist belt 154 and a back waist belt 156. The front and back belts 154, 156 may comprise a first extensible material and a second extensible material. An elastic member, such as an elastic film or a plurality of elastic strands, may be positioned intermediate the first extensible material and the second extensible material. The front waist belt 154 or the back waist belt 156 may comprise the elastic printed laminates disclosed herein. The front and back waist belts 154, 156 may also comprise at least a third material, such as a nonwoven material. In an example, the front and back waist belts may comprise a first extensible nonwoven material, a second extensible nonwoven material, and a plurality of elastic strands intermediate the first and second nonwoven materials. The first extensible nonwoven material or the second extensible nonwoven material may comprise a repeating graphic set. The first waist belt 154 and the second waist belt 156 may be attached on their lateral edges to each other to form side seams 158. The side seams may comprise butt seams or overlaps seams.

The central chassis 152 may comprise a topsheet, a backsheet, an absorbent core positioned at least partially intermediate the topsheet and the backsheet. The central chassis 152 may comprise an outer cover nonwoven material forming a garment-facing surface of the absorbent article and in a face-to-face relationship with the backsheet. The central chassis may comprise one or more acquisition layers and/or one or more distribution layers intermediate the topsheet and the absorbent core.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method for manufacturing a printed laminate on an absorbent article manufacturing line, the method comprising:
    conveying a first extensible material toward a point of joinder in a machine direction while straining the first material in the machine direction at a first strain, wherein the first extensible material comprises a plurality of repeating graphic sets, and wherein the plurality of repeating graphic sets each comprise a repeating graphic set length;
    separately, conveying a second extensible material toward the point of joinder in the machine direction while straining the second material in the machine direction at a second strain, wherein the second strain of the second extensible material is different than the first strain of the first extensible material by at least 0.5% and less than 3%;
    measuring at least some of the plurality of repeating graphic set lengths using a sensor upstream of the point of joinder while the first extensible material is under the first strain;
    comparing the repeating graphic set length to a predetermined laminate pitch;
    adjusting the first strain until the repeating graphic set length corresponds to the predetermined laminate pitch; and
    joining the first material and the second material at the point of joinder to form a printed laminate comprising the first extensible material and the second extensible material.

2. The method of claim 1, comprising conveying an elastic member toward and through the point of joinder intermediate the first extensible material and the second extensible material to form an elastic printed laminate.

3. The method of claim 2, wherein the elastic member comprises a plurality of elastic strands.

4. The method of claim 3, wherein the first extensible material comprises a nonwoven material, and wherein the second extensible material comprises a nonwoven material.

5. The method of claim 1, wherein one of the first and second extensible materials comprises a film.

6. The method of claim 1, wherein the first strain of the first extensible material is in the range of about 0% to about 2.5%.

7. The method of claim 1, wherein the second strain of the second extensible material is in the range of about 0.5% to about 3%.

8. The method of claim 1, wherein the second strain of the second extensible material is constant.

9. The method of claim 8, wherein the first strain is variable to adjust the repeating graphic set length.

10. The method of claim 1, comprising applying adhesive to the elastic member, to the first extensible material, and/or to the second extensible material upstream of the point of joinder.

11. The method of claim 1, comprising conveying the first extensible material over a roller upstream of the point of joinder, wherein the adjusting the first strain step comprises varying the rotational speed of the roller to increase or decrease the first strain of the first extensible material to shorten or lengthen the repeating graphic set length.

12. The method of claim 1, comprising cutting the printed laminate to the predetermined laminate pitch.

13. The method of claim 1, comprising joining the printed laminate with a portion of an absorbent article chassis downstream of the point of joinder.

14. A method for manufacturing a printed laminate on an absorbent article manufacturing line, the method comprising:
conveying a first extensible material toward a point of joinder in a machine direction while straining the first material in the machine direction at a first strain, wherein the first extensible material comprises a plurality of repeating graphic sets, and wherein the plurality of repeating graphic sets each comprise a repeating graphic set length;
separately, conveying a second extensible material toward the point of joinder in the machine direction while straining the second material in the machine direction at a second strain, wherein the second strain is different than the first strain;
measuring at least some of the plurality of repeating graphic set lengths using a sensor upstream of the point of joinder while the first extensible material is under the first strain;
comparing the repeating graphic set length to a predetermined laminate pitch;
adjusting the first strain until the repeating graphic set length corresponds to the predetermined laminate pitch;
conveying a plurality of elastic strands toward the point of joinder;
joining the first material and the second material at the point of joinder to form a printed elastic laminate comprising the first extensible material, the second extensible material, and the plurality of elastic strands, wherein the plurality of elastic strands are positioned intermediate the first extensible material and the second extensible material; and
joining the printed elastic laminate with a portion of an absorbent article chassis downstream of the point of joinder.

15. The method of claim 14, comprising conveying the first extensible material over a roller upstream of the point of joinder, wherein the adjusting the first strain step comprises varying the rotational speed of the roller to increase or decrease the first strain to shorten or lengthen the repeating graphic set length.

16. The method of claim 14, wherein the first extensible material comprises a nonwoven material, and wherein the second extensible material comprises a nonwoven material.

17. The method of claim 14, wherein the second strain is constant.

18. The method of claim 17, wherein the first strain is variable to adjust the repeating graphic set length.

19. A method for manufacturing a printed laminate on an absorbent article manufacturing line, the method comprising:
conveying a first extensible nonwoven material toward a point of joinder in a machine direction while straining the first material in the machine direction at a first strain, wherein the first extensible nonwoven material comprises a plurality of repeating graphic sets, and wherein the plurality of repeating graphic sets each comprise a repeating graphic set length;
separately, conveying a second extensible nonwoven material toward the point of joinder in the machine direction while straining the second material in the machine direction at a second strain, wherein the second strain is greater than the first strain, and wherein the second strain is constant, and wherein the second strain is in the range of about 0.5% to about 3%;
measuring at least some of the plurality of repeating graphic set lengths using a sensor upstream of the point of joinder while the first extensible material is under the first strain;
comparing the repeating graphic set length to a predetermined laminate pitch;
adjusting the first strain until the repeating graphic set length corresponds to the predetermined laminate pitch;
conveying a plurality of elastic strands toward the point of joinder; and
joining the first material and the second material at the point of joinder to form a printed elastic laminate comprising the first extensible material, the second extensible material, and the plurality of elastic strands, wherein the plurality of elastic strands are positioned intermediate the first extensible material and the second extensible material.

20. The method of claim 19, wherein the second strain of the second extensible material is different than the first strain of the first extensible material by at least 0.5% and less than 3%.

* * * * *